United States Patent
Krumme et al.

(10) Patent No.: US 7,274,765 B2
(45) Date of Patent: Sep. 25, 2007

(54) ROTATING DATA TRANSMISSION DEVICE FOR MULTIPLE CHANNELS

(75) Inventors: Nils Krumme, Feldafing (DE); Herbert Weithmann, Munich (DE); Harry Schilling, Eichstaett (DE); Stephan Lindorfer, Munich (DE); Georg Lohr, Eichenau (DE)

(73) Assignee: Schleifring und Apparatebau GmbH, Fuerstenfeldbruck (DE)

( * ) Notice: Subject to any disclaimer, the term of this patent is extended or adjusted under 35 U.S.C. 154(b) by 269 days.

(21) Appl. No.: 11/169,150

(22) Filed: Jun. 28, 2005

(65) Prior Publication Data

US 2006/0007766 A1 Jan. 12, 2006

(30) Foreign Application Priority Data

Jun. 28, 2004 (DE) .................... 10 2004 031 272

(51) Int. Cl.
 *A61B 6/00* (2006.01)
(52) U.S. Cl. ........................... 378/15; 378/210
(58) Field of Classification Search .............. 378/4–20, 378/210; 370/229, 235, 464; 375/141; 714/699, 714/746, 758
See application file for complete search history.

(56) References Cited

U.S. PATENT DOCUMENTS 6,292,919 B1   9/2001   Fries et al. ................. 714/758

OTHER PUBLICATIONS

Advanced Micro Devices, Am7968/Am7969, TAXIchip™ Integrated Circuits, Apr. 1994, pp. 1-49.

*Primary Examiner*—Courtney Thomas
(74) *Attorney, Agent, or Firm*—Kevin L. Daffer; Daffer McDaniel, LLP

(57) ABSTRACT

A device for signal transmission in computer tomographs comprising a rotating part supported to be rotatable with respect to a stationary part. A transmission controller is provided on the rotating part for compiling, from video data of a video source and from control information of a control unit, serial data for transmission to the stationary part by means of a rotary joint. A receiving controller is provided in the stationary part for receiving the serial data transmitted by the rotary joint and for evaluating these data and communicating the control information contained therein to a control unit, and the video data to a data sink. The serial data generated by the transmission controller comprise data frames, and video data and control information each being transmitted in a data frame.

15 Claims, 2 Drawing Sheets

ROTATING DATA TRANSMISSION DEVICE FOR MULTIPLE CHANNELS

PRIORITY CLAIM

This application claims priority to German Application No. 102004031272.9 filed Jun. 28, 2004.

BACKGROUND OF THE INVENTION

1. Field of the Invention

The invention relates to an electrical rotating data transmission device, especially for use in computer tomographs. In this, a transmission of digital image data obtained by an X-ray detector is effected without contact between a rotatable gantry and a stationary part of a computer tomograph. Furthermore, data also may be transmitted in the opposite direction to control the rotatable gantry.

2. Description of the Prior Art

According to known prior art, image data are transmitted via a broadband data path that is preferably non-contacting, whilst relatively slow control and monitor data are transmitted via separate slip-ring paths having a smaller bandwidth. For this, two independent transmission technologies are employed with a large attendant technical outlay. Further development of this prior art is disclosed in U.S. Pat. No. 6,292,919. In this, a data transmission of video data is effected by means of a TAXI chip set. This chip set is described in the data sheet "TAXIchip Integrated Circuits, Transparent Asynchronous Transmitter/Receiver Interface Am7968/Am7969" by Advanced Micro Devices (AMD), 1994. The chip set consists of a transmitter having a parallel-serial converter for converting parallel data to a serial data stream, and a receiver for converting the serial data stream to parallel data. An encoding of the data for transfer is effected by means of a 4B/5B code. With this 4B/5B encoding, an additional redundancy is introduced into the data stream. Thus, 8 Bit data words are converted to 10 Bit data words for transmission. With this, the two additional bits are not contained in the data stream at fixed given positions, but are used for forming additional codes which may be transmitted in addition to the codes needed for representing the data. Some of these additional codes are designated as command codes and may be triggered by separate control inputs on the TAXI chip set. A receiver is equipped to signal a receipt of such codes. Other codes are used for error recognition and are recognized as being inadmissible.

Now, according to the cited prior art, in some computer tomographs command codes adapted to be triggered by separate control inputs are utilized for signaling additional states (view start commands). By intelligent evaluation of the TAXI-chipset in the receiver, the control codes are recognized as such, and the presence of such a control code is signaled as a view start command to units connected to the receiver. At the same time, a data clock as is usually issued upon receipt of data is not issued, so that an erroneous evaluation of control codes as being data, made by units connected to the receiver, is not possible. With this prior art it is disadvantageous that the proposed signaling procedure can be effected exclusively by means of TAXI chips from the semiconductor manufacturer AMD. Parallel/serial converters as usually employed for communication do not have available any control inputs for emitting additional signaling codes.

BRIEF SUMMARY OF THE INVENTION

The invention is based on the object of advancing the known prior art so that, in addition to video data, additional signal communications can be transmitted within a defined time-grid, even with conventional parallel-serial converters.

According to the invention, this object is achieved by a device for signal transmission in computer tomographs, comprising:
- a rotating part supported to be rotatable with respect to a stationary part;
- a video source on the rotating part for generating video data from measurement data of a detector;
- a first control unit on the rotating part for generating control information;
- at least one transmission controller on the rotating part for generating, from the video data of the video source and from control information of the control unit, serial data for transmission to the stationary part by means of a rotary joint having a first data path;
- at least one reception controller on the stationary part for receiving and evaluating serial data transmitted by the rotary joint, and for communicating control information and video data contained in the serial data transmitted by the rotary joint to a second control unit and a data sink, respectively; and
- wherein serial data generated by the transmission controller comprise data frames, and video data and control information are transmitted in a common data frame.

According to the invention, the above object is also achieved by a computer tomograph comprising:
- a rotating part supported to be rotatable with respect to a stationary part;
- a video data source on the rotating part for generating video data from measurement data of a detector;
- a first control unit on the rotating part for generating control information;
- at least one transmission controller on the rotating part for generating, from the video data of the video data source and from control information of the control unit, serial data for transmission to the stationary part by means of a rotary joint;
- at least one reception controller on the stationary part for receiving and evaluating serial data transmitted by the rotary joint, and for communicating control information and video data contained in the serial data transmitted by the rotary joint to a second unit and a data sink, respectively; and
- wherein serial data generated by the at least one transmission controller comprise data frames, and video data and control information are transmitted in a common data frame.

According to the invention the above object is also achieved by a method for transporting data in a computer tomograph from a rotating part to a stationary part, comprising the steps of:
- generating video data from measurement data of a detector on the rotating part;
- reading the video data into a transmission controller;
- generating control information with a first control unit on the rotating part;
- reading the control information into the transmission controller;
- using the transmission controller to compile the video data and the control information to form common data frames;

issuing the data frames as serial data for transmission to the stationary part via a rotary joint, receiving the serial data on the stationary part from the rotary joint;

evaluating the data frames contained in the received serial data for control information and video data;

issuing control information contained in the serial data to a second control unit; and issuing video data contained in the serial data to a data sink.

DESCRIPTION OF THE DRAWINGS

In the following the invention will be described by way of example, without limitation of the general inventive concept, on examples of embodiment with reference to the drawings.

DETAILED DESCRIPTION OF THE INVENTION

Figure 1:
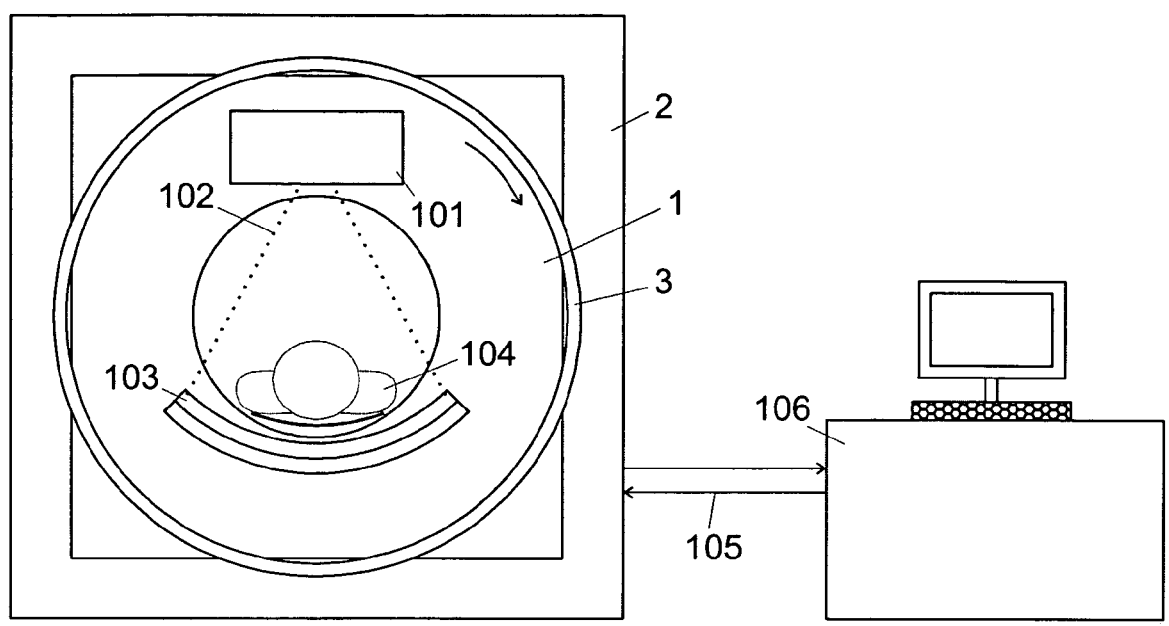
FIG. 1 shows an example of a device according to the invention.

FIG. 1 shows an example of a device according to the invention. A computer tomograph (CT scanner) consists of two main mechanical components. A stationary part 2, in which a rotating part 1 rotates, serves as a base and a support of the entire instrument. A patient 104 is positioned on a rest within an opening of the rotating part. An X-ray tube 101 and, opposite to it, a detector 103 are disposed for scanning the patient by means of X-rays 102. The X-ray tube 101 and the detector 103 are disposed to be rotatable on the rotating part 1. A rotary joint 3 serves as an electrical connection between the rotating part 1 and the stationary part 2.

With this, high electrical power for feeding the X-ray tube 101 is transmitted in the direction of the rotating part 1, and simultaneously video data are transmitted in the opposite direction. A communication of control information in both directions is provided in parallel to this. An evaluation and control unit 106 serves for operation of the computer tomograph, and also for displaying produced images. Communication with the computer tomograph is effected via a bidirectional link 105.

Figure 2:
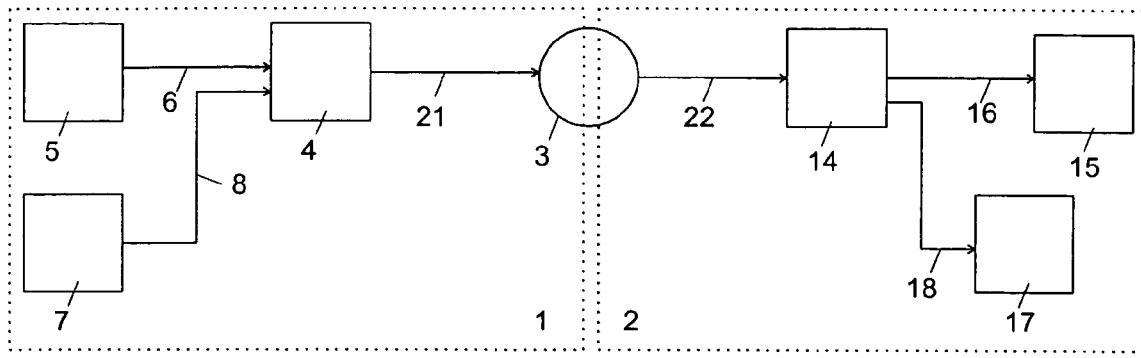
FIG. 2 shows in a schematic form a block circuit diagram of a device according to the invention.

FIG. 2 shows a block circuit diagram of a device according to the invention. The rotating part 1 comprises a data source 5 for generating video data 6 from measurement data from a detector 103. Furthermore, a control unit 7 is provided for generating control information 8. The video data 6 and also the control information 8 are supplied to a transmission controller 4 for generating serial data 21. These serial data 21 are now transmitted from the rotating part 1 via the rotary joint 3 to the stationary part 2 in the form of a stream of serial data 22. This is evaluated by a reception controller 14, so that from it may be gained video data 16 for a data sink 15, for example in the evaluation and control unit 106, and also control information 18 for a stationary control unit 17.

Figure 3:
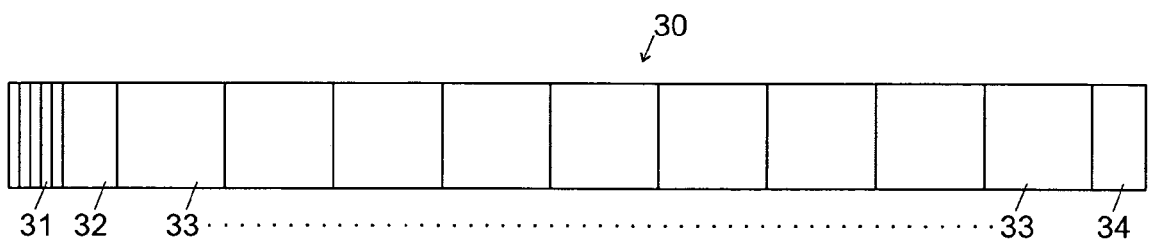
FIG. 3 shows a typical data frame as used for communication in the device according to the invention.

FIG. 3 shows a typical data frame 30 for transmission between the rotating part 1 and the stationary part 2, or in the opposite direction. A header 31 stands at the beginning of the data frame, for example to enable a receiver circuit to synchronize with the data clock. The header is followed by another data field containing, for example, status information 32 and possibly one or more addresses of one or a plurality of receivers, or of an originator, or optionally containing information on the distribution or the priority of the frame. Similarly, information on the number or the size of sub-frames 33 may be contained here. This field is now followed by the actual payload of the data frame in the form of one or a plurality of sub-frames 33 which are terminated by a trailer to signal the end of the data frame. This trailer 34 may also contain further status information and, in particular, a check sum (CRC).

The invention relates to a device for use in computer tomographs. Computer tomographs of this kind comprises a rotating part 1 that is supported for rotation relative to a stationary part 2. A data source 5, usually an X-ray detector on the rotating part, generates video data at a high data rate for transmission to a data sink 15 on the stationary part. Furthermore, at least one control unit 7 is provided on the rotating part, the serial data from which must be transmitted to a suitable control unit 17 on the stationary part. In most cases, even bidirectional communication is necessary between these two control units. Usually a rotary joint 3 having one or a plurality of physical transmission channels serves for transmitting the data.

A device in accordance with the invention comprises a transmission controller 4 for compiling data 6 generated by the data source 5 to form data frames 30. Furthermore, additional information is inserted into a data frame by this transmission controller as control information 8, in order to signal specific conditions. In order to achieve a real-time capability with an exactly defined reaction time, it is necessary for the data frames 30 to be of a defined size and a defined structure. For this, the control information 8 is preferably contained at given positions within the data frames. A data frame 30 of this kind typically comprises a header 31, additional status and log information 32, and also, as payload data, the video data, control information etc. Which are preferably transmitted in a plurality of sub-frames 33. A trailer following the payload data advantageously contains also a check sum 34. In accordance with the invention, the control information 8 can now be transmitted optionally within the scope of the status information 32, or even better within or as one of the sub-frames 33. It is of special advantage for this information to be transmitted in the first of the sub-frames 33.

Of particular advantage is a dynamic adaptation of the size of the data frames 30 according to the information to be transmitted, for example, in order to optimize the transmission at different resolutions or at different scan speeds. Thus, for example, a data frame could contain the data of a whole image, or even of only one detector line. For this, however, it is essential that at least during a given time interval a large number of data frames of the same construction be transmitted. A time interval of this kind may correspond, for example, to a transmission of a single image, but even better, to a transmission of a whole scan. These data frames also may be divided into further sub-frames. For this, it is of special advantage for the size or the structure of the sub-frames to be dynamically adapted to the respective transmission requirements.

Alternatively, data frames of different sizes may be fed into the data stream. This would be indicated, for example, for short control sequences, or short communications of high priority. The size of these data frames may be adapted to the purpose of the transmission. However, preferably fixed given sizes are used.

In another advantageous embodiment of the invention, redundant information is additionally inserted into the data frames 30 or the sub-frames 33. This redundant information could be employed not only for error correction (CRC). In addition, this information could be used also for conforming the data stream to the transmission characteristics of the data path. Thus, by means of a suitable design of the data frames, or of a suitable encoding of a data stream, certain spectral ranges preferably could be made use of, whilst the spectral power density in other ranges is reduced. This is of particular advantage when applied with transmission paths having a band pass or a low pass characteristic. Similarly, a broadening of a spectrum may be achieved in order to satisfy requirements made on interference emission, for example, as specified by EN 55011.

Furthermore, the additional information could serve to improve the synchronization of the receiver. If a check sum is already being transmitted in at least one sub-frame 33 containing control information 8, then the status information may be evaluated before the remainder of the frame is received. The same applies to a redundant encoding of the previously mentioned data frame, for example by means of 4B/5B.

Similarly, additional information such as test data, for example, for determining the bit error, may continue to be communicated.

Preferably, the transmission controller 4 is adapted to form a serial data stream 21. In another advantageous embodiment, the transmission controller 4 is adapted to generate a plurality of serial data streams. In this, data streams preferably relate to the same clock of a reference clock generator. Of particular advantage is a generation of the data streams at the same clock frequency. Similarly, different data streams may be also generated to conform to different data paths, advantageously being generated from the same basic clock frequency by division or multiplication. With a generation of a plurality of serial data streams, a plurality of data having a reduced bandwidth may be used for transmission. Thus, not only can a plurality of economic data paths which have a small bandwidth and operate in parallel be employed instead of an expensive broadband data path. At the same time, the total availability of the transmission system can be increased by using a plurality of parallel data paths. Thus, for example, the data may be divided equally, or according to channel capacity of the data paths. Thus, in a particularly advantageous case a separate data path may be used for each detector row. Alternatively, the data may be transmitted simultaneously via two data paths, in order to afford greater reliability of transmission, or a possibility of error correction.

Basically, with a device according to the invention, a plurality of data streams can be transmitted in parallel or alternately. Data streams of this kind may originate, for example, from different data sources or different image-forming methods.

Furthermore, as an alternative, a multiple transmission of certain data may be made, because of the higher available data rate. Particularly with data for which safety is of high relevance, this makes possible an especially high reliability of transmission. Thus, for example, video data having large data volumes could be subject to multiple transmissions for reasons of reliability.

In advantageous manner a means for switching-over a data stream and/or data streams between different data paths of the rotary joint 3 may provided This is advantageously incorporated in the transmission controller. A switching-over facility makes it possible, for example in the case of a defective data path, to switch to another functioning data path.

The clock frequencies or data rates of the data streams are preferably conformed to known standards of telecommunication or network technology, so that components of particularly favorable cost may be employed. Similarly, the clock frequencies or data rates may be also conformed to the processing capacity of the control computers or their backplanes used in the rotating or stationary part. Alternatively, the clock frequencies could be also optimized to the employment of further components of favorable cost, such as, for example, CRD (clock and data recovery) chips, PLL or quartz crystals.

In another advantageous embodiment of the invention, means for compressing the image data before their transmission via the serial data path is provided, preferably in the transmission controller. With this compression means, the data volume to be transmitted may be reduced. For this, it is of advantage for the additional control information not to be involved in the compression. This is unnecessary, because not only is the information content of the additional control information only relatively small, and the data volume to be transmitted therefore comparatively low. Apart from this, the compression and the decompression require computing time which of necessity is not deterministic. Therefore, a signaling in real time is possible only with an uncompressed transmission of the control signals. However, it is not to be excluded that with a development of future new compression algorithms, a compression of the control signals, and particularly incorporation into the data stream of the video signals, will become possible. A suitable means for decompression is provided on the stationary side, preferably in a reception controller.

In most cases bidirectional communication between the control unit 7 disposed on the rotating part, and the control unit 17 disposed on the stationary part, in necessary. For this, both the transmission controller 4 and also the reception controller 14 make available a virtual bidirectional data path for control data. In addition to the above-described transmission of the control data from the rotating part 1 to the stationary part 2, a transmission in the opposite direction is advantageously effected by means of a further non-contacting data path preferably adapted to a lower data rate. This also is administrated by the transmission controller 4 and in the reception controller 14. Thus, the reception controller 14 undertakes an emission of control data of the stationary control unit 17 via this further non-contacting data path to the transmission controller 4 which relays the data to the rotating control unit 7. Because of this common administration of both directions by the transmission controller 4 and the reception controller 14, the control units 7 and 17 need not distinguish between transmission in the different directions and a corresponding control of different data paths.

Optionally, a loop-back-test also may be provided, in which, for example, test data generated from the stationary side are transmitted to the rotating side and are sent back from there. Now from these, the transmission quality may be determined, for example by comparison with the originally sent data.

In another advantageous embodiment of the invention for communication between the rotating part 1 and the stationary part 2, a circular bus system is used. In a circular bus system of this kind, the data are transmitted whilst circulating between the rotating part and the stationary part. Optionally, further subscribers may be incorporated in the circular bus. The data frames on the data path from the rotating part 1 to the stationary part 2 preferably contain video data and also control information 8. In the opposite direction, the payload of the data packages may consist of configuration information and further control data. Similarly, the previously transmitted video information can be transmitted back to the rotating part 1 for a check on transmission errors. In most cases the rotary joint 3 is equipped with non-symmetrical data paths. Thus, in most cases the data rate from the rotating part 1 in the direction towards the stationary part 2 is substantially higher than the data rate in the opposite direction. With this, preferably a non-symmetrical circular bus may be formed. Thus, for example, a typical size of a data frame from the rotating part 1 to the stationary part 2 may be substantially larger than that of a data frame in the opposite direction, because here the payload is also substantially larger owing to the video signals. Nevertheless, an isochronous or even synchronous transmission is possible, because for this, only data frames by themselves are needed, without dependence upon their payload.

In another embodiment of the invention, inadmissible codes are transmitted, or artificial transmission errors generated, in order to signal particular conditions, such as, for example, a resetting of the bus system.

The device described here can be used to advantage not only with rotating data transmission systems, but also with linear transmission systems, such as are employed, for example, for controlling transport vehicles, or in crane systems. Furthermore, the device according to the invention can be used not only for computer tomographs, but also for other rotating applications, such as, for example, for communication with radar antennae.

With computer tomographs a rotating-fixed transmission path and a fixed-rotating transmission path are provided in each case. In a general case, the described invention may also be used in a direction opposite to that illustrated, because this is only a matter of reference to location.

Further subject matter of the invention is a design of a computer tomograph comprising a rotating part 1 that is supported to be rotatable with respect to a stationary part 2. A rotary joint 3 is provided for transmitting video data 6 of a high data rate from a data source 5 to a data sink 15 on the stationary part, and also serial data of a control unit 7 of the rotating part to a control unit 17 of the stationary part. This rotary joint may, if necessary, comprise a plurality of transmission channels. Furthermore, a transmission controller 4 is provided for compiling the data 6 generated by the data source 5 to form data frames. With this transmission controller, additional information is inserted into a data frame as control information 8 for signaling specific conditions.

A method for transporting data in a device according to the preamble of claim 1 comprises the following steps: at first the video data 6 and also other control information 8 are read into a transmission controller 4. The video data 6 read-in here, and also the control information 8, are now compiled to form common data frames 30. These data frames are issued as serial data 21 for transmission via a rotary joint.

Following a receipt of the data transmitted by the rotary joint 3 as serial data 22 by a reception controller, the data frames 30 contained therein are evaluated, and the control information 18 contained therein is in turn issued to a control unit 17, and the video data 16 is issued to a data sink 15.

According to another aspect of the invention, the rotary joint has at least two signal paths. Additionally or as an alternative, at least two rotary joints with at least one signal path are provided. Such a configuration will be considered herein as one rotary joint having several signal paths. The data, whether being video data or control data, is multiplexed into several signal paths. By this way, the overall bandwidth can be significantly extended. In previous systems usually one high speed signal path (e.g. 1 Gigabit/s) was used for transfer of video data while a low speed signal path (e.g. 10 Megabit/s) was used for control data. Now, video and control data are multiplexed together into several high speed data paths. This could be for example 2 data paths with 1 Gigabit/s each, doubling the overall capacity of the system to 2 Gigabit/s. This solution requires about the same space as the old system, but has a much higher flexibility. So doubling of control data rate would require a new signal path for 20 Megabit/s instead of 10 Megabit/s, while at a multiplexed 2 Gigabit/s only an increase of 1% is necessary, which could in most cases be done by modifying data assembly and framing.

Further according to the invention, at least one of the rotary joints or data paths referenced above comprises an electrical, optical or RF-Link or a combination thereof, like an electro-optical link. Electrical links comprise all direct contacting links like sliprings and also contactless links. Optical links comprise all links using light as a medium, having either a direct optical contact or using some reflecting, diffracting or other transfer member like waveguides, etc. to couple light from a transmitter to a receiver. RF-links comprise all links based on high frequency signals, having either a direct radiation coupling or a transmission via lines or waveguides.

The invention claimed is:

1. A computer tomograph, comprising:
    a rotating part supported to be rotatable with respect to a stationary part;
    a video data source on the rotating part for generating video data from measurement data of a detector;
    a first control unit on the rotating part for generating control information;
    at least one transmission controller on the rotating part for generating, from the video data of the video data source and from control information of the control unit, serial data for transmission to the stationary part by means of a rotary joint;
    at least one reception controller on the stationary part for receiving and evaluating serial data transmitted by the rotary joint, and for communicating control information and video data contained in the serial data transmitted by the rotary joint to a second control unit and a data sink, respectively; and
    wherein serial data generated by the at least one transmission controller comprise data frames, and video data and control information are transmitted in a common data frame.

2. A device for signal transmission in computer tomographs, comprising:
    a rotating part supported to be rotatable with respect to a stationary part;
    a video data source on the rotating part for generating video data from measurement data of a detector;
    a first control unit on the rotating part for generating control information;
    at least one transmission controller on the rotating part for generating, from the video data of the video data source and from control information of the control unit, serial data for transmission to the stationary part by means of a rotary joint having a first data path;
    at least one reception controller on the stationary part for receiving and evaluating serial data transmitted by the rotary joint, and for communicating control information and video data contained in the serial data transmitted by the rotary joint to a second control unit and a data sink, respectively; and wherein serial data generated by the transmission controller comprise data frames, and video data and control information are transmitted in a common data frame.

3. The device according to claim 2, wherein the data frames comprises at least one sub-frame.

4. The device according to claim 3, wherein control information and video data are transported in respective separate sub-frames.

5. The device according to claim 2, wherein the data frames are of a size that can be adapted to information to be transmitted.

6. The device according to claim 3, wherein the sub-frames are of at least one of a size and a number that can be adapted to information to be transmitted.

7. The device according to claim 3, wherein the data frames or the sub-frames contain redundant additional information serving for correction of errors, or for adaptation to characteristics of a transmission path.

8. The device according to claim 2, wherein the transmission controller is adapted to form a plurality of serial data streams, and the receiving controller is correspondingly adapted to receive a plurality of serial data streams.

9. The device according to claim 2, wherein a means for compressing payload data, preferably the image data, before their conversion to serial data is provided in the transmission controller, and a corresponding means for decompression is provided in the reception controller.

10. The device according to claim 2, wherein at least one second data path for signal transmission from the stationary part to the rotating part is provided in the rotary joint, the at least one second data path being administrated on a rotating side by the transmission controller, and on a stationary side by the reception controller.

11. The device according to claim 2, wherein the device is configured as a circular bus.

12. The device according to claim 2, wherein said first data path is based on an electrical, optical or RF-Link or a combination thereof.

13. A device for signal transmission in computer tomograph, comprising:

a rotating part supported to be rotatable with respect to a stationary part;

a video data source on the rotating part for generating video data from measurement data of a detector;

a first control unit on the rotating part for generating control information;

at least one transmission controller on the rotating part for generating, from the video data of the video data source and from control information of the control unit, serial data for transmission to the stationary part by means of a rotary joint having at least two paths;

at least one reception controller on the stationary part for receiving and evaluating serial data transmitted by the rotary joint, and for communicating control information and video data contained in the serial data transmitted by the rotary joint to a second control unit and a data sink, respectively; and wherein at least one of video data and control information is multiplexed into at least two paths of said rotary joint.

14. The device according to claim 13, wherein at least one of said data paths is based on an electrical, optical or RF-Link or a combination thereof.

15. A method for transporting data in a computer tomograph from a rotating part to a stationary part, comprising the steps of:

generating video data from measurement data of a detector on the rotating part;

reading the video data into a transmission controller;

generating control information with a first control unit on the rotating part;

reading the control information into the transmission controller;

using the transmission controller to compile the video data and the control information to form common data frames;

issuing the data frames as serial data for transmission to the stationary part via a rotary joint;

receiving the serial data on the stationary part from the rotary joint;

evaluating the data frames contained in the received serial data for control information and video data;

issuing control information contained in the serial data to a second control unit; and issuing video data contained in the serial data to a data sink.

* * * * *